United States Patent [19]

Sano et al.

[11] 4,377,752
[45] Mar. 22, 1983

[54] SCINTILLATION CAMERA RADIATION SHIELDING

[75] Inventors: Richard M. Sano, Stamford; John W. Steidley, North Haven; Bruce M. Gillespie, New Haven; Jack B. Tinkel, Durham, all of Conn.

[73] Assignee: Picker Corporation, Cleveland, Ohio

[21] Appl. No.: 114,380

[22] Filed: Jan. 22, 1980

Related U.S. Application Data

[63] Continuation of Ser. No. 917,071, Jun. 19, 1978, abandoned.

[51] Int. Cl.³ .................................................. G21F 5/04
[52] U.S. Cl. ................................... 378/152; 250/505.1
[58] Field of Search ............... 250/505, 510, 511, 512, 250/513, 515, 363 S

[56] References Cited

U.S. PATENT DOCUMENTS

| | | | |
|---|---|---|---|
| 3,474,250 | 10/1969 | Jelatis et al. | 250/515 |
| 3,631,249 | 12/1971 | Friede et al. | 250/505 |
| 3,792,274 | 2/1974 | Larson | 250/363 S |
| 3,849,649 | 11/1974 | Carey | 250/511 |
| 3,980,407 | 9/1976 | Hill | 250/511 |

*Primary Examiner*—Bruce C. Anderson
*Attorney, Agent, or Firm*—Watts, Hoffmann, Fisher & Heinke Co.

[57] ABSTRACT

A radiation absorption shield assembly is disclosed for controlling the configuration of the radiation sensitive field of a radiation detecting camera. The shield assembly includes a first annular lead shield element defining a first aperture and mounted to the camera for blocking out a fixed field of radiation. The assembly also includes a second annular lead shield element in series with the first which defines a second aperture movable with respect to the first aperture. Attached to and in a spaced parallel relation with the first shield element is a circular radiation transparent disk which defines a thin gap to accommodate the second shield element. The second shield element is slidably adjustable within the gap, transverse to the first element, by one conducting a radiation study, to vary the configuration of a region of interest defining a field area through which radiation can pass from the patient for detection by the camera.

14 Claims, 5 Drawing Figures

SCINTILLATION CAMERA RADIATION SHIELDING

This is a continuation of application Ser. No. 917,071 filed June 19, 1978, abandoned.

BACKGROUND OF THE INVENTION

1. Field of the Invention

This invention relates to a radiation shield for covering a portion of a radiation detection camera's field, thereby limiting radiation detection to that from a region which is of interest to the camera user and to allow the camera to better resolve structure in the region of interest by relieving it of the need to process data from background regions of no interest.

A gamma or scintillation camera is typically used in diagnostic analysis of certain parts of the human body. A radioactive substance is administered to a patient and by determining the local and intensity of the radiation as it is emitted from the body, an image of internal structure of the body is obtained.

Typically, the camera remains stationary with respect to the patient while a representation of the spatial distribution of radioactivity is developed. With many of these cameras, a relatively large disk shaped scintillation crystal is positioned to be stimulated by radiation emitted from the patient. In most cameras, a collimator is interposed between the patient and the crystal so that, for example, with a parallel hole collimator, the rays striking the crystal are all generally perpendicular to it.

The crystal scintillates as it converts gamma energy impinging on it to light energy. The light is conducted through a suitable light pipe, to an array of phototubes. When a photo tube is stimulated by light generated in a crystal by a scintillation an electrical signal is emitted which is proportional to the intensity of light energy received by that tube. When a scintillation causes several of the photo tubes to emit signals, these signals are emitted concurrently and are then summed to provide a signal known as the "Z" signal. This "Z" signal is conducted to a pulse height analyzer to determine whether the signal reflects the currents of a so-called photo peak event of the isotope which has been administered to the patient. That is, the "Z" signal is of appropriate strength to reflect the conversion of the energy of a gamma ray emitted from the administered isotope to light energy by the crystal.

Summing and ratio circuits are also provided which develop what are known as "X" and "Y" signals. These "X" and "Y" signals cause a dot to be produced on the screen of the oscilloscope at a location corresponding to the location of the detected scintillation. Thus, the oscilloscope dots are displaced relatively, each at a location corresponding to the location of the corresponding scintillation in the crystal and the oscilloscope dots are integrated to produce an image. Suitable circuits for producing an oscilloscope image of spatial distribution of a radioactive isotope are known.

The photo tubes, the circuits, and the oscilloscope function in a unit to provide a light amplifier such that each dot produced on the oscilloscope represents a scintillation. Through the use of a persistence screen on the scope, or a photographic camera, these dots are integrated to produce an image.

While it is known that certain radioactive substances tend to localize in a given tissue of the body, those substances may collect in areas that are not of interest to the physician for the study being conducted. Thus, in a heart study, for example, radioactive material may collect in the lungs. In observing the image from the gamma camera, the physician is only interested in radiation images coming from the heart and has no interest in radiation coming from the lungs. It would therefore be advantageous to eliminate signals coming from the lungs or any other area of the body not of interest.

It would also be beneficial to block out unwanted radiation in order to improve spatial resolution in the gamma camera image by enhancing the information density for improved image quality. When a scintillation occurs in the detecting crystal it produces an electrical signal. During the time in which the imaging electronics is responding to one radiation count, it cannot process signals indicating the presence of another photon impinging upon the photon crystal. This down or dead time is primarily a result of the processing circuitry's inability to handle two different signals simultaneously. If radiation coming from an area not of interest to the physician causes the scintillation crystal to produce a signal, the radiation coming from the region of interest cannot be processed by the scintillation counter electronics during the ensuing "dead" time. This down time or period in which meaningful radiation detection cannot occur results in a loss of spatial resolution in the final image of radiation in the region of interest.

In studies where the radioactive count rate is measured, the electronic circuitry down time can adversely affect count rate accuracy. A cardiac bypass study, for example, provides a quantitative measure of a subject's heart output. If radiation emitted from outside the heart area is processed, the efficiency in recording scintillations caused by radiation coming from the heart is diminished. This inefficiency occurs because the imaging electronics cannot process all signals coming from the heart if it must process signals from outside that region of interest.

2. Prior Art

In the past, this problem was dealt with by requiring the patient to wear a specially designed leaded garment, having appropriately configured openings, to shield radiation coming from areas of the body not of interest. This technique was awkward and required many variously designed heavy shield garments for various regions of interest corresponding to parts of the body.

SUMMARY OF THE INVENTION

The present invention provides a new and improved method and apparatus for screening out or shielding radiation from irrelevant areas of the patient's body during a scintillation camera study. By selectively screening out unwanted incoming radiation, the down time or dead time of the camera is diminished, allowing more complete processing of signals associated with the region of interest.

The device is directly attached to the scintillation camera and is adjustable depending upon what area of the body is to be observed. The device effectively blocks out gamma rays coming from an area of the body of no interest to the physician. In this way, the scintillation camera can produce improved images from the region of interest within a patient's body, because it is relieved of processing much background information of no interest. The camera can also provide more accurate quantitative counting from the region of interest since it is not forced to process signals outside that region of interest. This improved accuracy is maintained for count rates higher than those which could be processed by the unshielded camera.

One embodiment of the invention includes a radiation absorption shield for use in conjunction with a radiation detection camera including a first radiation attenuating device defining a first aperture, and being fixed relative to the camera. A second radiation attenuating device defining a second aperture, and movable with respect to the first radiation attenuating device. The second element is supported by a structure which maintains it movable in a plane generally transverse to the propagation of the radiation to the camera.

More specifically, the first radiation attenuating structure preferably effectively absorbs all radiation impinging upon it, except for that which passes through its aperture. The first radiation attenuating means defines a constant area aperture through which radiation coming from an area of interest can pass. The second radiation attenuating structure allows the physician to selectively eliminate radiation coming from an area of the body of no interest by adjusting the configuration of the combined final field area through which radiation can pass, as defined by the relative locations of the superposed apertures. The shield assembly is directly attached to the gamma or radiation camera, thereby obviating need for cumbersome and unweildy shielding garments used heretofore.

One embodiment of the invention that has been found useful employs two annular disks of different aperture size which can be moved relative to each other to cooperatively block radiation coming from areas other than the physician's area of interest. One of the annular disks is adjustable with respect to the other and is readily movable by the user of the shield. The movable disk may include a handle arrangement whereby the disk can be moved through the area being irradiated and thereby selectively adjusting the configuration of the gamma ray flux.

In a slightly different configuration of the shield, a radiation absorbing material defines a variable aperture whose center coincides wth the gamma camera field. In this arrangement the diameter of the variable aperture is selectively varied depending upon what region of interest the physician is observing.

In one preferred arrangement, the movable annular disk for attenuating radiation is supported by a clear "Lexan" plastic shield which is supported by the gamma camera. The movable lead shield is coated with a surface of "Teflon" which allows the annular shield to easily slide over the surface of the supporting "Lexan" structure.

From the above it is apparent that one object of the present invention is to provide a means for selectively attenuating radiation from an area of the subject patient which is of little or no interest to the doctor. This is achieved by the use of a lead shield device directly attached to the gamma camera which blocks out an unwanted portion of the camera's field of view and enhances the image of a region of interest.

It is another object of the invention to provide an adjustable attenuating device. This allows the physician to manually tailor the configuration of the gamma or scintillation camera while he is conducting a scan.

These and other features and objects of the present invention will become better understood when considered in conjunction with the detailed description of the invention and the accompanying drawings.

DETAILED DESCRIPTION

Figure 1:
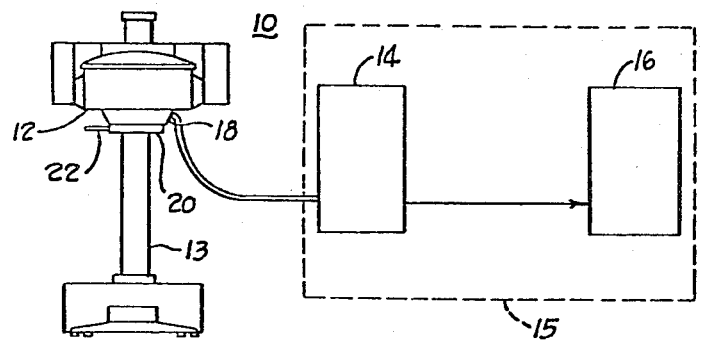
FIG. 1 depicts a gamma camera system utilizing the shield which comprises the present invention.

Shown generally in FIG. 1 is a gamma camera system 10 for observing radiation patterns emanating from within a patient or subject. The patient is prepared by injecting a given amount of radioactive material into the body and monitoring the progress or motion of that radioactive material in the body. A typical gamma camera study might involve the study of the functioning and structure of the heart. To achieve this study a radioactive substance would be injected directly into the patient's vascular system and the movement of the radioactive material would be studied with the gamma camera system 10.

The gamma camera system comprises a detector unit 12 mounted on a movable mount structure 13. One suitable gamma camera is known as the "Dyna Camera 4" produced by the assignee of the present invention. The gamma camera sends imaging signals to a module 15 which includes imaging electronics 14 and a display 16. Attached to the detector unit 12 is a collimator 18 which serves to direct the incoming gamma rays in a parallel direction. Directly attached to the collimator 18 is a radiation absorption shield assembly 20 comprising the present invention. Seen protruding from the shield 20 is a handle 22 for selectively adjusting the shield operation.

In operation, gamma rays are emitted by the radioactive substance that has been injected into the patient and impinge upon the detector unit 12. Before reaching the detector unit, however, the rays encounter both the shield 20 and the collimator 18. The collimator 18 tends to direct parallel rays to the detector unit and the shield assembly 20 serves to block off a portion of the incident radiation.

Figure 2:
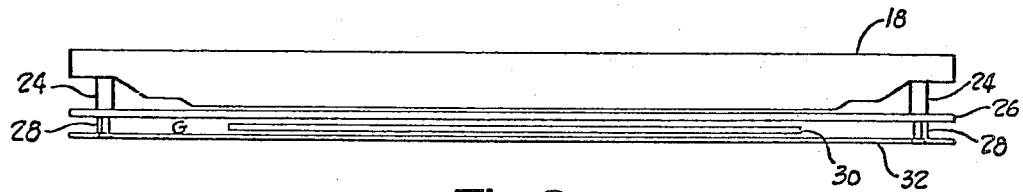
FIG. 2 is an elevated view of the shield shown in FIG. 1.

FIG. 2 displays how the radiation shield 20 of FIG. 1 is mounted to the collimator 18. The detector unit has been omitted from FIG. 2 but the gamma camera collimator 18 is shown on the upper portion of the diagram. First 26 and second 30 radiation attenuating elements are shown in close proximity to the gamma camera collimator 18. The first radiation attenuating element is directly attached to the collimator by suitable fasteners. The arrangement of FIG. 2 includes spacers 24 which separates the collimator from the first attenuating device. This separation prevents the warping of the attenuating device due to pressure from the collimator.

A support device 32 is shown separated from the first attentuating means by a means of a second spacer 28. The second spacer 28 in conjunction with the support device 32 defines a gap G between the first attenuating device 26 and the support structure 32. The second radiation attenuating device 30 is inserted into the gap G and is movable about the gap to alter the amount of radiation reaching the gamma camera. As seen in FIG. 2, the first and second radiation attenuating devices are generally parallel to each other and also transverse to the direction of radiation travel from the patient to the detector, i.e., parallel to the axis of the detector field. Both the first and second radiation attenuating devices include apertures (as seen in FIGS. 4 and 5 discussed in detail below) for allowing the radiation from the source to pass to the gamma camera.

Figure 3:
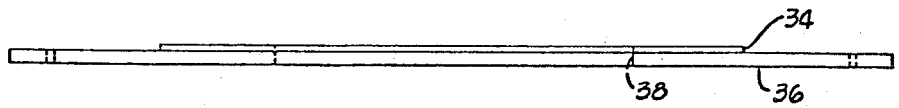
FIG. 3 illustrates a portion of the apparatus shown in FIG. 2.
Figure 4:
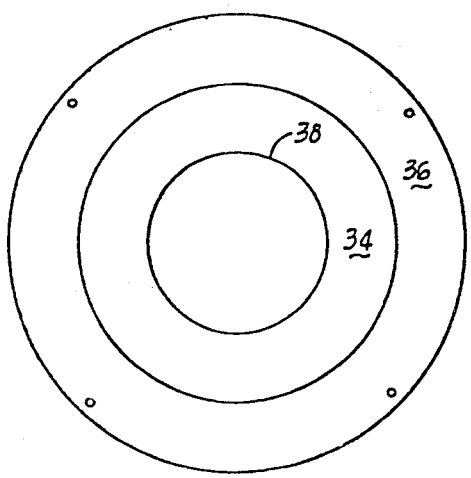
FIG. 4 is a top view of one portion of the shield of FIG. 2.
Figure 5:
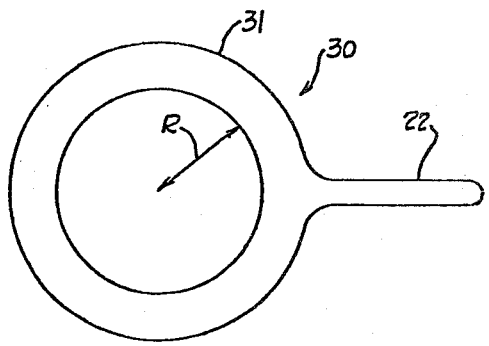
FIG. 5 is a top view of a second portion of the shield of FIG. 2.

FIGS. 3 and 4 show the first radiation attenuating device which is directly attached to the collimator 18 by means of a suitable fastener and displaced from the collimator by a spacer 24. FIG. 3 is an enlarged cross-sectional view of the first attenuating device of FIG. 2. FIG. 4 is a view of the first radiation device as seen from above. The first attenuating device includes two annular disks of different materials with a common sized aperture in the middle.

The smaller of the two annular disks 34 is made from lead and serves to attenuate the radiation coming from the source. It is the purpose of this lead shield to reduce the operative area of a typical gamma camera from a value of approximately 15 inches in diameter to 10 inches in diameter. In one embodiment the lead shield has an inside diameter of 10 inches and an outside diameter of 17 inches. Since a typical gamma camera has a field of 15 inches in diameter the lead disk will overlap the field slightly on each side of the camera.

The lead disk is attached to an aluminum disk 36 which is directly attached to the collimator 18. The aluminum disk also contains a 10 inch diameter aperture but has an outside diameter substantially larger than the lead disk. The aluminum material provides support structure for the lead disk and also provides a convenient method for attaching the lead disk to the gamma camera collimator 18. In one embodiment the outside diameter of the aluminum disk is 25½ inches in diameter and is attached to the collimator by means of four screws which are evenly spaced about the aluminum disk and located approximately 1 inch inside the outside diameter of that disk.

As seen in FIG. 3 the lead and aluminum disks 34, 36 co-act to form a layered annular arrangement with one constant area circular aperture 38. The lead material disk is positioned above the aluminum disk. In one embodiment both the lead and aluminum disks are approximately 1/16 inch thick.

As seen in FIG. 2, directly attached to the aluminum portion of the first attenuating device is a Lexan shield 32 which serves as a support for the variable or second attenuating device. The "Lexan" shield is a circular disk of diameter identical to the outside diameter of the aluminum disk which forms a portion of the first attenuating device. It provides a support for the variable or movable second attenuating device and could be of any construction which would provide this function. In one typical arrangement the shield comprises a ¼ inch sheet of 25½ inch diameter "Lexan" plastic.

FIG. 5 is a top view of the second or variable attenuating device. This second attenuating device includes an annular disk portion 31 the aperture of which has a radius R which may be equal to, greater than, or smaller than the aperture radius of the first attenuating device. In a typical embodiment, the aperture of the second attenuating device woud be smaller than the aperture of the first attenuating device.

Although as seen in FIG. 5, the second attenuating device appears to be one disk structure, it is actually a layered disk structure comprised of two different materials. One of the materials is lead and forms an annular disk for attenuating the radiation impinging upon that disk. The other disk is an aluminum annular arrangement for providing structure to the disk attenuating device. Attached to the aluminum portion of the disk is a handle arrangement 22 which allows a physician to manually adjust the position of the aperture which allows radiation to pass to the gamma camera. The handle structure may conveniently be cut from one piece with the disk arrangement or may be cut separately and welded on to the disk arrangement. Preferably several second attenuating devices can be provided, each having a different sized aperture. Three suitable aperture diameters are 4, 6, and 8 inches.

In operation, the second attenuating device 30 is moved across the camera field and relative to the first attenuating device to vary the position of gamma rays being sent to the gamma camera. Thus, by positioning the inside aperture of the second attenuating device it is possible for the physician to selectively screen out radiation coming from an area of no interest during the particular scan. The region of interest under study can then more effectively be examined since the gamma camera processing electronics need only process gamma camera scintillations coming from within the region of interest. To facilitate movement of the second attenuating device it is possible that the combined lead-aluminum attenuating device be coated with a teflon layer which facilitates movement of that device over the "Lexan" supporting structure.

According to a second embodiment of the invention it is possible that the second attenuating device be also fixed relative to the gamma camera and that the aperture size be varied depending upon the area to be studied by the use of known iris varying apparatus.

While the invention has been described with particularity, it should be appreciated that certain modifications and alterations may be made in the dimensions and components of the invention without departing from the spirit or scope of the invention as set forth in the appended claims.

What is claimed is:

1. In a gamma camera of the type having a detector including a receptor responsive to incident gamma radiation and circuitry for producing an image in a display, the improvement comprising:
    (a) a collimator connected to the detector for selectively allowing incident radiation from a patient to reach the receptor;
    (b) an apertured disc of radiation absorbing material functioning as a radiation attenuating device;
    (c) attenuating device support structure connected to the detector and delineating a disc receiving and supporting gap; and,
    (d) said disc being slidably positioned in the gap and movable in the gap across the camera field selectively to align the disc's aperture with a patient field of interest and to screen out and block the transmission of radiation emanating from locations without the field of interest to the receptor whereby to decrease camera down time which would otherwise to occasioned by such radiation emanating from without this field of interest.

2. The camera of claim 1 wherein there is a second attenuating device forming a part of the support structure and constructed of a material to screen and block out radiation.

3. A gamma camera for producing images representative of the spatial distribution of administered radiation emanating from a patient comprising:
   (a) a detector including a radiation responsive receptor;
   (b) a fixed, apertured, disc ring attenuator connected to the detector in alignment with the receptor;
   (c) the attenuator being formed of a radiation absorbent material adapted to screen and block the transmission of radiation to the receptor except through the attenuator aperture;
   (d) a movable apertured disc attenuator slidably positioned adjacent the fixed attenuator for selectively aligning the movable attenuator aperture with a portion of the fixed attenuator aperture by movement across the camera field whereby to delineate a portion of the receptor which will produce an image of a field of interest;
   (e) the movable attenuator being formed of an endless quantity of material surrounding the aperture and having radiation absorbent characteristics ample to screen and block the transmission of radiation coming from regions without a field of interest under investigation; and,
   (f) an attenuator support secured to the detector in predetermined spaced relationship with the fixed attenuator to define a movable attenuator supporting slot therebetween with the support being positioned sufficiently close to the fixed attenuator to retain the movable attenuator in an adjusted position but sufficiently spaced to permit its adjustment.

4. The camera of claim 3 wherein the movable attenuator includes an integrally formed radially projecting handle adapted to facilitate adjustive movement of a movable receptor.

5. The camera of claim 3 wherein there is a collimator carried by the detector and interposed between the fixed attenuator and the receptor in spaced relationship with fixed attenuator and wherein the movable attenuator receiving slot is on a side of the fixed attenuator opposite the collimator.

6. A process of operating a scintillation camera which includes a detector to increase the quantum of energy processed by the camera which emanates from a given field of interest and thereby improve the quality of an image of that field of interest comprising the steps of:
   (a) positioning a camera to conduct a study of a field of interest;
   (b) positioning a movable attenuator shaped to screen and block radiation between a portion of the detector and the field of interest;
   (c) adjusting at least a selected one of the attenuator and detector positions across the field of interest until the field of interest is substantially aligned with an unblocked portion of the detector and the attenuator is positioned to block the transmission of radiation emanating from without the field of interest to the detector; and,
   (d) thereafter developing an enhanced image of the field of interest.

7. A process of operating a scintillation camera which includes a detector to increase the quantum of energy processed by the camera which emanates from a given field of interest and thereby improve the quality of an image of that field of interest comprising the steps of:
   (a) positioning a camera to conduct a study of a field of interest;
   (b) positioning an apertured movable attenuator between a portion of the detector and the field of interest;
   (c) moving the attenuator relative to the detector across the field of interest until the field is substantially aligned with the attenuator aperture and the attenuator is positioned to block the transmission of radiation emanating from without the field of interest to the detector; and,
   (d) thereafter developing an enhanced image of the field of interest.

8. For use with a gamma camera adapted for making cardiac and other medical studies, an improved beam delineating attenuator assembly comprising:
   (a) a fixed apertured disc of a material adapted to block the transmission of gamma radiation emitted by a patient during a diagnostic study, the fixed disc being adapted to be fixedly connected to a gamma camera detector across the camera field of view and transverse to a path along which patient emitted radiation will travel during a study;
   (b) a movable attenuator support connected to the fixed attenuator in spaced relationship to define a movable attenuator supporting space therebetween; and,
   (c) a movable apertured disc slidably positionable in the space and movable transversely relative to the fixed disc to adjust a camera's field of view to include a region of interest the movable disc being formed of a material adapted to screen and block radiation emitted by a patient during a diagnostic examination.

9. The assembly of claim 8 wherein a selected one of the support and the discs includes a coating of a material which enhances the slidability of the movable disc in the space.

10. The assembly of claim 8 wherein the radiation blocking material of each disc surrounds the aperture.

11. The assembly of claim 8 wherein at least one of the disc apertures is circular.

12. The assembly of claim 8 wherein the movable disc includes a handle.

13. The assembly of claim 8 wherein there are a set of movable attenuators each of which has an aperture of a size different than the apertures of other discs of the set, and wherein only a selected one of the apertures is in the space at any given time.

14. The process of claim 6 further including the step of selecting the movable attenuator from a set of apertured attenuators each having an aperture of a size different than the aperture of another attenuator of the set.

* * * * *